US008512335B2

(12) United States Patent
Cheng et al.

(10) Patent No.: US 8,512,335 B2
(45) Date of Patent: Aug. 20, 2013

(54) HIGH FREQUENCY ALTERNATING CURRENT MEDICAL DEVICE WITH SELF-LIMITING CONDUCTIVE MATERIAL AND METHOD

(75) Inventors: Elbert T. Cheng, Los Altos, CA (US); Tai C. Cheng, Mountain View, CA (US); Jacqueline T. Cheng, Mountain View, CA (US)

(73) Assignee: Curo Medical, Inc., Saratoga, CA (US)

( * ) Notice: Subject to any disclaimer, the term of this patent is extended or adjusted under 35 U.S.C. 154(b) by 686 days.

(21) Appl. No.: 12/783,714

(22) Filed: May 20, 2010

(65) Prior Publication Data
US 2011/0288543 A1    Nov. 24, 2011

(51) Int. Cl.
*A61B 18/14* (2006.01)
(52) U.S. Cl.
USPC ............................. 606/41; 606/34
(58) Field of Classification Search
USPC .................. 606/32–35, 41, 48–50
See application file for complete search history.

(56) References Cited

U.S. PATENT DOCUMENTS

| 4,033,351 A * | 7/1977 | Hetzel ............................... 606/48 |
| 4,616,660 A | 10/1986 | Johns |
| 5,383,917 A * | 1/1995 | Desai et al. ..................... 607/102 |
| 5,462,546 A | 10/1995 | Rydell |
| 5,514,131 A | 5/1996 | Edwards et al. |
| 5,571,153 A | 11/1996 | Wallsten |
| 5,766,153 A * | 6/1998 | Eggers et al. ................... 604/114 |
| 5,916,213 A | 6/1999 | Haissaguerre et al. |
| 6,086,586 A | 7/2000 | Hooven |
| 6,132,426 A | 10/2000 | Kroll |
| 6,139,545 A | 10/2000 | Utley et al. |
| 6,168,593 B1 | 1/2001 | Sharkey et al. |
| 6,273,887 B1 | 8/2001 | Yamauchi et al. |
| 6,464,704 B2 | 10/2002 | Schmaltz et al. |
| 6,511,480 B1 | 1/2003 | Tetzlaff et al. |
| 6,585,735 B1 | 7/2003 | Frazier et al. |
| 6,632,193 B1 | 10/2003 | Davison |
| 6,770,072 B1 | 8/2004 | Truckai et al. |
| 6,802,843 B2 | 10/2004 | Truckai et al. |
| 6,843,789 B2 | 1/2005 | Goble |
| 6,923,806 B2 | 8/2005 | Hooven et al. |

(Continued)

OTHER PUBLICATIONS

International search report dated Mar. 1, 2011 for PCT/US2011/020136.

(Continued)

*Primary Examiner* — Michael Peffley
(74) *Attorney, Agent, or Firm* — Wilson, Sonsini, Goodrich & Rosati

(57) ABSTRACT

A high frequency alternating current medical device and method of using such is disclosed. High frequency alternating current medical device comprises a power source, an electric field generator, a self-limiting conductive material electrical component, at least one probe or needle-type projection, and at least two conductive segments located on probe or needle-type projection. At least two conductive segments are electrically connected to electric field generator so that an electric field is created between conductive segments, which induces an electrical current, which generates heat, and causes a certain desired precise cell injury. Self-limiting conductive material electrical component allows such precise cell injury because it limits electrical current through target tissue. Invention may be used in medical, dental, or veterinary applications. Exemplary embodiments include cosmetic applications, treatment of wrinkles, remodeling of subcutaneous tissue, treatment of muscle spasms, and others. Medical device can be small, hand-held, and easily manipulated to perform surgery.

24 Claims, 9 Drawing Sheets

(56) References Cited

U.S. PATENT DOCUMENTS

| | | |
|---|---|---|
| 7,070,597 B2 | 7/2006 | Truckai |
| 7,160,296 B2 | 1/2007 | Pearson et al. |
| 7,326,202 B2 | 2/2008 | McGaffigan |
| 7,517,349 B2 | 4/2009 | Truckai et al. |
| 7,887,535 B2 | 2/2011 | Lands et al. |
| 8,075,555 B2 | 12/2011 | Truckai et al. |
| 2003/0125735 A1 | 7/2003 | Herzon |
| 2010/0057083 A1 | 3/2010 | Hanna |
| 2011/0166563 A1 | 7/2011 | Cheng et al. |

OTHER PUBLICATIONS

Office action dated Jan. 22, 2013 for U.S. Appl. No. 12/652,262.

* cited by examiner

HIGH FREQUENCY ALTERNATING CURRENT MEDICAL DEVICE WITH SELF-LIMITING CONDUCTIVE MATERIAL AND METHOD

BACKGROUND OF THE INVENTION

1. Field of the Invention

This invention relates to electrosurgical devices. Electrosurgery is the application of a high-frequency electric current to tissue as a means to cut, coagulate, desiccate, or fulgurate tissue. Its benefits include the ability to make precise cuts with limited blood loss. Electrosurgery also includes surgical procedures where one or more localized portions of tissue are ablated using high frequency alternating current to generate heat, without heating other types of tissue near the target tissue. Electrosurgery devices use probe-like structures to physically contact the target tissue where such structure is a type of electrode acting to pass electrical current to the tissue. Electrosurgery devices typically cause substantial physical damage to tissue.

This invention applies an electrical field across target tissue, causing an electrical current to "conduct" across said target tissue. Heat is produced from this electrical current by ohmic or joule heating where the heat produced from such is proportional to the square of the amount of this current. A "lesion area" is created where tissue is heated above normal temperature. Heating occurs in a very controlled way where temperature of the lesion area does not rise above a maximum temperature. Carefully controlled heating provides the opportunity to cause a desired precise cell injury. The invention carefully controls heat generation in the lesion area with a self-limiting conductive material electrical component in electrical series connection with the electrical current in the target tissue. Self-limiting conductive material electrical component precisely controls the electrical current flowing across the target tissue.

Electrical current is directly proportional to heat production, which is directly proportional to temperature increase, where elevated temperature and duration of such, along with location and size of the lesion area, primarily determine the type and extent of cell damage, which, in turn, determines whether the desired precise cell injuries are attained. Thus, this invention uses precise current control to yield a precise minimum level of cell injury required to effect the desired result for the patient without going beyond this level, thereby effecting the result without unnecessary cell injury. All prior art electrosurgical devices and radio frequency medical devices cannot control temperature or heat production as precisely as this invention and thus cause more damage to target tissue.

The invention may be used in medical, dental, or veterinary applications. Exemplary embodiments of the invention have cosmetic applications including treatment of wrinkles and remodeling of subcutaneous tissue. Exemplary embodiments are also used for therapeutic applications including treatment of muscle spasmas and chronic pain and the control of one or more muscles of other target tissue. Exemplary embodiments are designed to specifically affect nerve tissue where the desired cell injury is to "deaden" the nerve or break the electrochemical connection, either temporarily or permanently, between nerve and muscle that causes nerve-to-muscle contractile function. However, this invention may be used to cause a desired precise cell injury to any type of cell or organ in the body within only the limitation of the relative sizes of the probes/needles on the invention apparatus as manufacturing technology changes with the times as compared to the size of the particular cells of interest, where cells may be of any type known human or otherwise.

2. Description of Related Art

A nerve is a cell that is relatively large. Each nerve cell contains a soma, multiple dendrites, an axon fiber, and multiple axon terminals. The soma is the central part of the nerve; it contains the nucleus of the cell. The soma can range from 4 to 100 micrometers in diameter. The axon and dendrites are filaments that extend outward from the soma. Many dendrites typically surround and branch off from the soma, and have length of up to a few hundred microns. The axon is a single cable-like projection extending outward from the soma that can extend over 100 times the diameter of the soma. The axon carries electrochemical nerve signals away from the soma to effectively control one or more muscles. Axon terminals are located opposite the soma-end of the axon. Typically, axon terminals terminate in a branch network of synapses, which release chemicals to communicate with one or more muscles or other tissue or with other dendrites or soma from another nerve cell within a chain of nerve cells leading to one or more muscles or other tissue.

Typically, a large number of axons from many cells are bundled together in a large conduit called an epineurium, with other nested conduits inside. Analyzing the physiological structure of these conduits, we start with an inner conduit or sheath called an endoneurium, which directly surrounds each axon. Multiple axons are typically grouped together into fasicles and further protected by a mid level sheath called a perineurium. Further, multiple perineurium bundles of axons are typically nested within an outer sheath called an epineurium. This is widely known in the art. Thus, each axon is protected by at least three sheath layers, i.e. an epineurium, a perineurium, and an endoneurium, going from outer most to innermost layer. Note that each large conduit or epineurium contains very many bundles of endoneurium conduits, thus it would be possible to sever completely the axons of some nerve cells, while leaving intact the complete endoneurium of other nerve cells.

This prompts a basic discussion of nerve cell injury. The Seddon system is a basic classification system used to describe nerve injury where there are three categories of injuries—neuropraxia, axonotmesis, and neurotmesis. The following is also well understood in the art.

With neuropraxia, the integrity of the axon is preserved so the endoneurium, perineurium, and epineurium are all intact, but there is an interruption in conduction of the electrochemical impulse traveling down the axon. This is the mildest form of nerve injury. Neuropraxia is typically a biochemical lesion caused by concussion injuries to the cell. There is a temporary loss of function, which is reversible within hours to months of the injury (the average is 6-8 weeks).

With axonotmesis, the integrity of the axon is interrupted but the endoneurium, perineurium, and epineurium are not punctured or deformed significantly. The result is typically loss of both motor and sensory functions, but with recovery through regeneration of the axon, a process that takes place at a certain rate per day, typically taking longer than neuropraxia for recovery. With neuropraxia and axonotmesis the intact endoneurium provides a guide for axonal regeneration where the nerve regenerates along the endoneural tubules.

Conversely, with neurotmesis, the integrity of the supporting structures are disrupted or punctured, disrupting axonal regrowth and reimplantation. Typically, the injury results from severe contusion, stretch, or laceration of the cell or other internal disruption of the cell architecture sufficient to involve the perturbation of the endoneurium, perineurium, or epineurium. Results are typically complete loss of motor, sensory, and autonomic function. Thus, the electrochemical signals do not complete the connection to the muscle or target tissue. Neurotmesis injury is typically permanent.

Comparably, a temporary type of neurotmesis results from nerve toxicity caused by local anesthetic, which is typically injected in or near a nerve cell. Anesthetic also disrupts the electrochemical signals sent to the muscle, thereby causing a loss of motor, sensory, and autonomic function. Botulinum toxin or Botox®, as used with the popular cosmetic procedure for wrinkles, is used as a neuromodulator that works at the neuromuscular junction to block the transmission between the nerve and muscle resulting in paralysis of the muscle to reduce wrinkles.

This invention is first to provide the ability to effect a wide range of cell injury from a minimum level of neuropraxia to full neurotmesis, through electrical current heating means, without also effecting large-scale physical damage in the target area. This invention can provide temporary effects or permanent relief to a patient without surface tissue cosmetic defects.

BRIEF SUMMARY OF THE INVENTION

The invention comprises a medical device and method of using such. Medical device comprises at least one probe or needle-type projection at its distal end and at least two conductive segments located on said at least one probe or needle-type projection. At least one probe or needle-type projection is capable being inserted into a body cavity or into body tissue, at which point also capable of conducting electrical current between said at least two conductive segments. In "one-probe or needle-type projection" mode, said at least two conductive segments are located on the one and only probe or needle-type projection. In "two-probe or needle-type projection" mode, one of said at least two conductive segments is typically located on each of the two probes or needle-type projections. Probes or needle-type projections are typically inserted into tissue or a body cavity containing the target cells or into nearby to such; then an electrical current is conducted between said segments to effect the desired precise cell injury. Probes or needle-type projections may be inserted into tissue, so that electrical current occurs subcutaneously. In this fashion, the heat-defined lesion area is entirely subcutaneous, resulting in minimal change of appearance on the surface of the tissue.

Medical device further comprises a power source capable of applying the appropriate electrical fields across said at least two conductive segments in order to generate the appropriate electrical current in the target tissue. The power source may be alternating current or direct current.

Best mode medical device further comprises an electric field generator capable of being powered by said power source and generating one or more electric fields across said at least two conductive segments. In best mode, electric field generator is small and miniaturized. Electric fields may be generated in continuous wave form, such as sine, triangular, or square wave or similar, and at various frequencies, intensities, and polarizations in order to yield the exact desired heating to cause the desired precise cell injury. Electric fields may be of a direct current pulse nature, as well, such as sine, triangular, or square wave or similar pulse shape. Electric field generator may emit several different shaped pulses and continuous wave forms at the same time. Electric field generator may be small enough to be handheld but also capable of supplying a 3-watt field into 150 ohms at 460 KHz using a hand-held direct current battery power source.

Medical device further comprises a self-limiting conductive material electrical component in electrical series connection with said electrical current passing through the target tissue. "Self-limiting conductive material" is defined as a material whose electrical resistive properties vary with its temperature. Self-limiting conductive material electrical component functions electrically like a thermistor, a thermocouple, or a switch in the electrical heating circuit of the target tissue. Self-limiting conductor material electrical component, in effect, controls the electrical current passing through the target tissue, and thus controls the temperature of the target tissue, and tissue surrounding target tissue.

Entire medical device may be small enough to be handheld. Power source, electric field generator, self-limiting conductive material electrical component, at least one probe or needle-type projection, and at least two conductive segments may be incorporated into one device, small and light enough to be comfortably held and very effectively handled by the surgeon to perform surgery.

BRIEF DESCRIPTION OF THE DRAWINGS

FIG. 6A also defines the blow-up view of FIG. 7.

FIG. 6B also defines cross-sectional plane 6A.

FIG. 6C also defines the blow-up view of FIG. 8.

Figure 1:
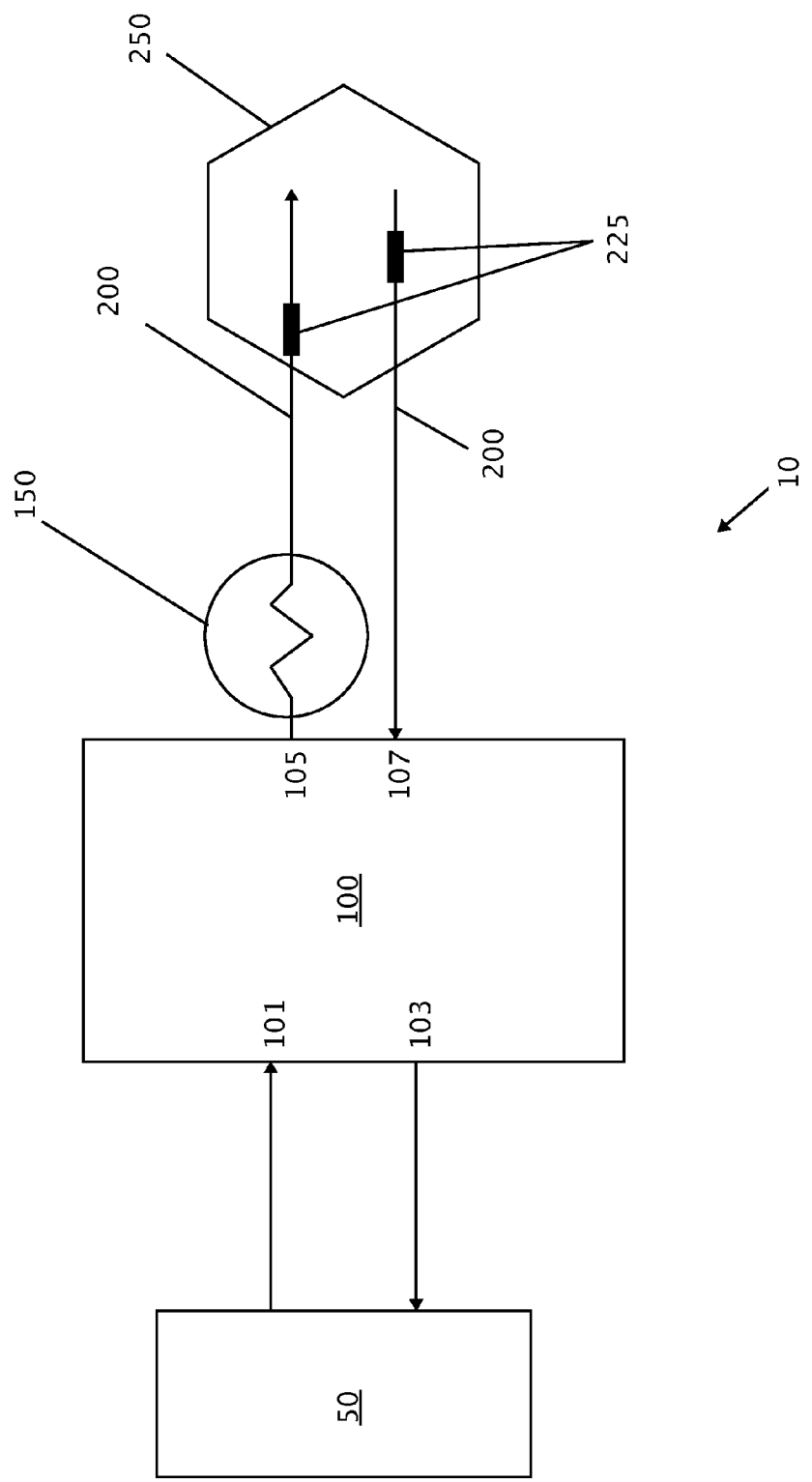
FIG. 1 is a circuit diagram of a basic mode of medical device with two probes or needle-type projections.

| DEFINITION LIST | |
|---|---|
| Main Term | Definition |
| 10 | Medical Device |
| 20 | User Interface |
| 21 | Main Power on/off Switch |
| 23 | Electric Field on/off Switch |
| 25 | Power Indicator Light |
| 27 | Electric Field Indicator Light |
| 50 | Power Source |
| 75 | Removably Attachable Surgical Tip for Medical Device |
| 100 | Electric Field Generator |
| 101 | Power Input Positive |
| 103 | Power Input Negative |
| 105 | At Least One Phase Signal Output |
| 105a | Transformed 105 Signal |
| 107 | At Least One Common Signal Output |
| 107a | Transformed 107 Signal |

-continued

DEFINITION LIST

| Main Term | Definition |
| --- | --- |
| 109 | Trimmer Input |
| 111 | Trimmer Input |
| 125 | Control Module |
| 127 | Frequency Modulation Control |
| 129 | Current Cut-off Setting |
| 150 | Self-limiting Conductive Material Electrical Component |
| 175 | Transformer |
| 200 | At Least One Probe or Needle-type Projection |
| 225 | At Least Two Conductive Segments on 200 |
| 250 | Target Tissue |

DETAILED DESCRIPTION OF THE INVENTION

A power source 50 is required to generate the electric field between a set of at least two conductive segments (conductive segments) 225. Power source 50 may directly generate the electric field between conductive segments 225 or alternatively power source 50 may indirectly power an electric field generator 100, which in turn generates the electric field between conductive segments 225. Power source 50 may be a direct current or an alternating current power source. In the case of a direct current power source 50, the electric field generator 100 would be required to produce alternating current or alternating polarity electric fields in the target tissue 250. Best mode power source 50 is a direct current battery because there are many standard sizes of such batteries that are small in size but also capable of powering a special electric field generator device capable of producing the appropriate electric fields resulting in the desired precise cell injury.

Alternating current, as opposed to direct current, is preferred because alternating current can produce more heat per amp than direct current in this situation. There appears to be a particular resonance frequency or spike frequency where heat production is maximized from alternating current travelling across a particular type of target tissue 250. At this frequency, current passes through the target tissue 250 with the least resistance. Thus, at a particular resonance frequency of a particular target cell, less power is required to produce the same or more heat in that cell. This design is preferred because it reduces the power requirements of the device, and thereby allows the device to be small enough to be hand-held. The resonance frequency of nerve cells and their surrounding tissue is 460 KHz and thus is the best mode frequency. There are prior art electrosurgical devices that operate at this frequency because this frequency appears to be the resonance frequency of many types of tissue, not just nerve tissue.

Electric field generator 100 comprises a pulse width modulation power supply electrically connected to common circuit board components including resistors, capacitors, diodes, and switches. Electric field generator 100 may further comprise a transformer 175, where the output signals from said pulse width modulation power supply are the primary connections with said transformer. Electric field generator 100 is typically custom designed to generate a specific alternating polarity field, with a specific frequency and power, in order to function properly with the specific probe/extension 200 of device 10 according to the requirements to yield the specific desired precise cell injury. In the case of best mode electric field generator 100, extensive development was expended to yield an electric field generator 100 that is appropriate for nerve cells using a three-needle probe 200 where the generator was also designed to be of a very small size. Best mode electric field generator 100 includes said pulse width modulation power supply and circuit board components assembled onto a custom circuit board, of a overall long and narrow shape such as rectangle, that is capable of fitting inside of an enclosure of the shape and size of a typical pen as depicted on FIGS. 5-8. Alternately, electric field generator 100 may consist of many electrical circuit boards that are electrically connected by loose wires to fit inside of various differently shaped enclosures. Best mode electric field generator 100 includes a doughnut shaped transformer 175 electrically connected to the distal end of said custom circuit board with the distal end inside the doughnut hole of transformer 175, where the secondary voltage and current from transformer 175 is passed through the target tissue 250.

Best mode pulse width modulation power supply comprises at least six electrical connections: two power input connections consisting of positive and negative power connections 101 and 103; two signal output connections 105 and 107; and two trimmer input connections 109 and 111. Output signals 105 and 107 create electric fields in the target tissue located between conductive segments 225 in rapidly changing alternating polarity in order to generate or induce the alternating current in the target tissue. Current is generated or induced because tissue contains water and other conductive molecules to allow electrical current to take place in response to the electric fields. Output signals 105 and 107 are electrically processed through said custom circuit board before electrically connecting with conductive segments 225. The frequency of the alternating polarity of the electric fields largely matches that of the frequency of the alternating currents created thereby. Alternately, outputs 105 and 107 may be electrically connected to the primary inputs on transformer 175, where secondary outputs of transformer 175 are 105a and 107a. Transformer 175 can be used to help stabilize resonance frequency on the target tissue, filter out switching noise from generator 100, and extend battery life of device 10 by operating generator 100 at more efficient frequency than resonance 460 KHz pertaining to nerve tissue. Further, electrically processed signal from 105, 105a, 107, or 107a may be looped back to a control unit 125, as discussed below, where signals are further processed and returned back to inputs 109 and 111 on best mode electric field generator 100.

Electric field generator 100 is also capable of emitting one or more direct current pulses from 105 or 107 into target tissue 250 in order to provide nerve detection and precise location of high frequency alternating current medical device prior to heat production. Before the surgeon generates the alternating current field that heats target tissue 250, the surgeon could locate the precise target nerve cell or component thereof using the one or more direct current pulses. Direct current pulses may be of various sizes and shapes where multiple shaped pulses may be emitted from the electric field generator 100 at the same time. The surgeon may position the at least two conductive segments on or into the overall area of the target cell and then emit the pulse or pulses from conductive segments. When one of the pulses is electrically connected to the target nerve cell, the pulse stimulates the muscle that the nerve drives, thereby causing said muscle to twitch or move in some way. Thus, a step of searching for the exact target cell and then and step of final positioning of 200 and 225 may be used to improve precision and accuracy of the surgery to yield the desired precise cell injury. Searching occurs until the sought after muscle twitches or otherwise the correct movement is witnessed, at which point the surgeon knows the correct nerve cell or component thereof has been located and that the at least two conductive segments are now precisely located on the exact target tissue 250. Thus, high frequency alternating current medical device 10 can be very precise and accurate because the at least two conductive segments are known to be exactly located correctly by detecting and identifying the precise location of high frequency alternating current delivery to achieve ablation of nerve tissue. At this point, the surgeon may then actuate the alternating current electrical field to cause exact target tissue heating where no heating is done to any other tissue.

Best mode electric field generator 100 is small and miniaturized so that it may be easily held in one hand by the average adult person. Considerable research and development has been accomplished to achieve an electric field generator 100 in such small size. This is the first hand-held radio frequency generator for use in an electro surgery device. Small size was primarily achieved by significant numbers of prototype and testing cycles aimed at reducing power requirements while still achieving desired precise cell injury. As a result, only a standard 9-volt battery is required to power current best mode electric field generator 100 in order to achieve the desired precise cell injury.

Figure 1A:
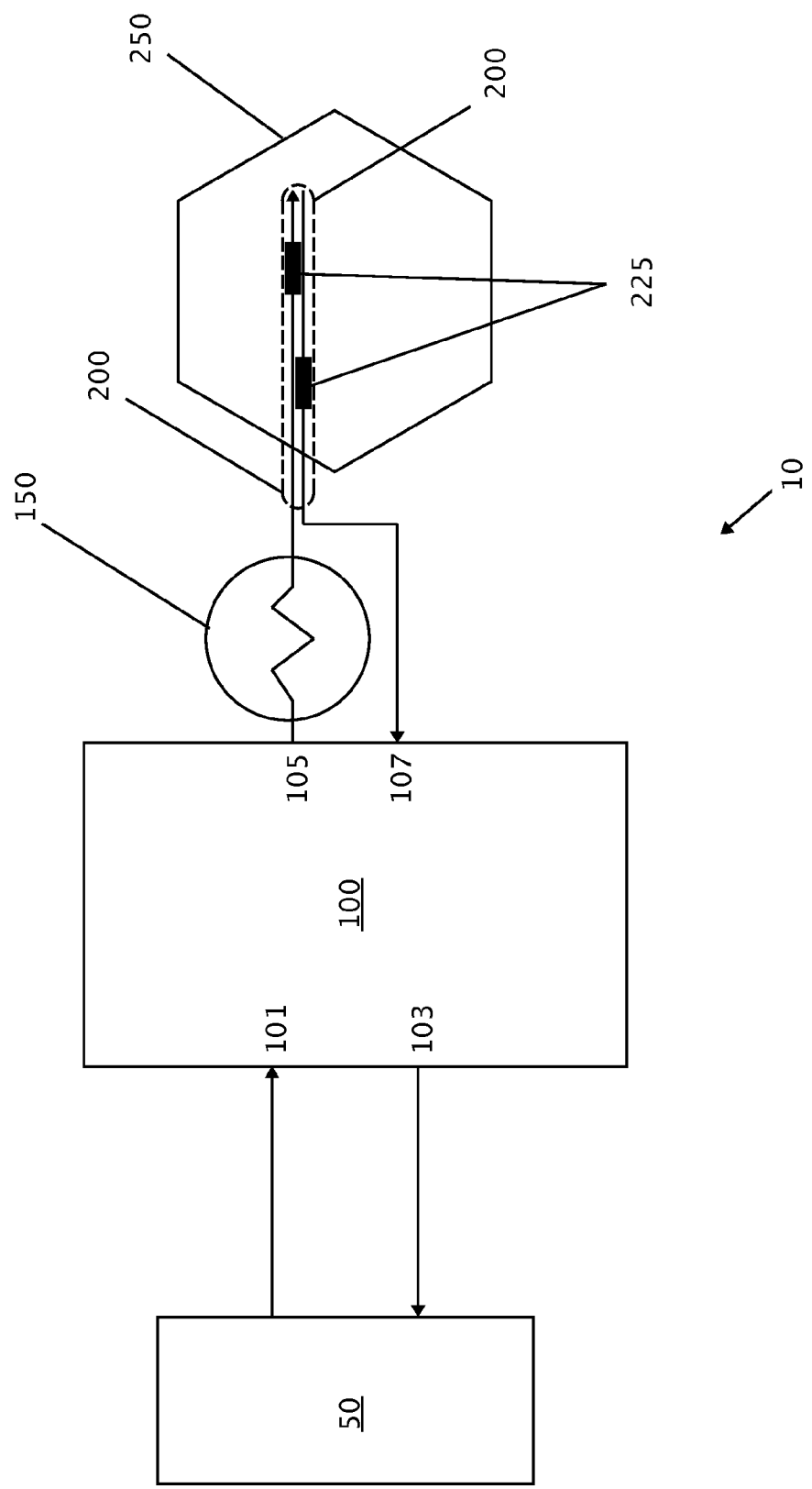
FIG. 1A is a circuit diagram of a basic mode of medical device with one probe or needle type projection.

In a basic mode, high frequency alternating current medical device 10 would have two probes or needle-type projections 200 and the electric field generated by 100 would be single phase. A circuit diagram for this mode is depicted in FIG. 1. One probe or needle-type projection 200 would include one segment 225 electrically connected to contact 107 and the other probe or needle-type projection 200 would include the other segment 225 electrically connected to contact 105. In another basic mode, high frequency alternating current medical device 10 would have one probe or needle-type projection 200 and the electric field generated by 100 would be single phase. A circuit diagram for this mode is depicted in FIG. 1A. The single probe or needle-type projection 200 would include both segments 225. In more complicated modes, device 10 could have many more projections 200 and thus electric field generator 100 would need to have at least an equal number of signal outputs to utilize the many projections, each electrically connected to one probe or needle-type projection 200. For instance, each projection could emit one of many phase signals or one of many common signals produced by the generator, leaving possibility for a device 10 with very many probes or needle-type projections 200 to create intricate electric field combinations to help yield very specific desired precise cell injury. Or, device 10 could have many probes or needle-type projections 200 with only two signal outputs 105 and 107, where 105 and 107 signals are connected to the many projections in alternating fashion, perhaps along a row or arc of projections 200. Alternating only two signals in this fashion can create a large lesion area along the row or arc from only a one-phase alternating electric field because current is created between each projection 200 in this fashion.

Figure 2:
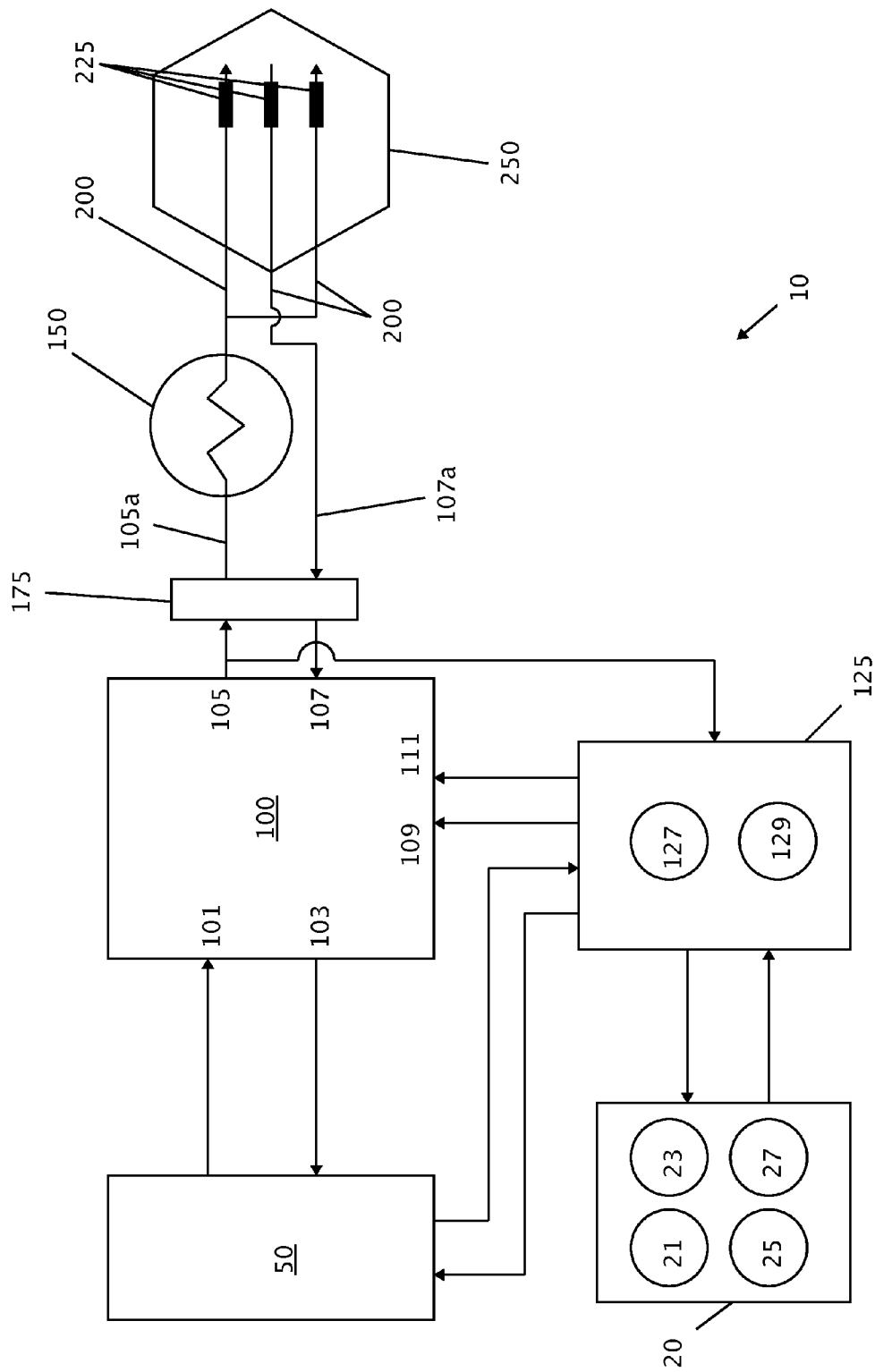
FIG. 2 is a circuit diagram of best mode of medical device.

Best mode high frequency alternating current medical device 10 has three needle-type projections arranged in a line. See FIGS. 7 and 8. The center projection 200 is electrically connected to common signal 107 or 107a, generated by electric field generator 100. The two outer projections are electrically connected in parallel to a single-phase signal 105 or 105a, generated by electric field generator 100. A circuit diagram for best mode is depicted in FIG. 2. In all arrangements and modes, it is the phase signal that passes through the self-limiting conductive material electrical component 150 before entering the target tissue.

At least one probe or needle-type projection 200 may be removably attachable to the rest of high frequency alternating current medical device 10. Further, there may be a wide range of removably attachable at least one or needle-type projections 75, 200 of many different types, sizes, shapes, materials, etc. that are removably attachable to the rest of high frequency alternating current medical device. Thus, the invention includes a series of removably attachable tips 75, where each tip 75 comprises: at least one needle of projection 200 and at least two conductive segments 225 located thereon, where each is electrically connected to the rest of the device according to circuit diagrams on FIGS. 1-2 when attached onto medical device.

One such removably attachable tip 75 may be another nerve finder with two small pads on the distal end. Two small pads are used to electrically connect the surface of the target tissue to the electric field generator 100. Thus, the nerve finder tip 75 may be first used to find a nerve where another tip 75 would then be attached to heat the nerve once found.

Best mode removably attachable tip 75 is removably attachable to the distal end of high frequency alternating current medical device 10. Best mode removably attachable tip 75 is of a general conical shape or cup shape with an opening on the wide end of the cone and a flat call member on the narrow end of the cone to form an overall cup shape, where at least one needle-type projection 200 is attached to the exterior surface of the narrow end of the cone or bottom of cup. The distal end of high frequency alternating current medical device 10, with tip 75 removed, may also have a general conical shape or cup shape, where device cone is slightly smaller than tip cone. Thus, the concave tapered section of tip 75 may then slide onto the convex tapered section of the device cone, where tip 75 snuggly fits onto device cone. Further, there may be a securing mechanism such as a clasp means, snap means, lock means, or similar to hold tip 75 onto the device cone in a very stable and secure fashion, so that surgery can be performed by the surgeon. Said securing mechanism would also have a release means so that removably attachable tip 75 may be removed. Thus, clasp means, snap means, lock means, or similar would have capability of releasing said means to remove tip 75. For instance with snap means, tip cone may be of a flexible nature to allow finger squeezing to cause deformity in tip cone thereby releasing one or more snap points between tip cone and device cone. Specific attachment means is not critical to patentability. When tip 75 is snapped into place onto device 10, an electrical connection occurs between at least two conductive segments 225 and generator signals 105 or 105a and 107 or 107a. Removably attachable tips 75 may be supplied in a sterile condition and then disposed of after use.

The operating frequency of the pulse width modulation power supply can be adjusted within about five percent using either trimmer input connection 109 or 111. In best mode, trimmer input connections 109 and 111 are electrically connected to a control module 125. See FIG. 2. Control module 125 is powered by battery 50 and is electrically connected to electric field generator 100. Control module 125 includes one or more trimmer resistors or similarly functioning electronic components that are electrically connected to a frequency modulation control switch 127, which is a setting switch on the control unit 125 used to adjust the frequency of signal 105. This is manual frequency adjustment.

Control module 125 may also automatically fine-tune and stabilize the frequency of signal generated by 100 by sampling signal 105 and electrically processing it to determine whether the frequency is optimum. Signal and current from 105 is electrically filtered, processed, and analyzed where the result yields a signal input to adjust trimmer input 109 or 111. Thus, control unit creates a feedback circuit from signal output 105 to trimmer input 109, which results in automatic fine-tuning and stabilization of output. Control unit 125 uses special arrangements of common circuit board components to custom design the automatic feedback control circuit design. In the case of more than one output phase signal, a feedback circuit may have to be created for each output phase in order to properly automatically fine-tune and stabilize frequency of all phases. Control unit 125 also determines if current through the target tissue is above a certain maximum preset limit and shuts down its electric field generation when said current goes beyond this limit. This is current cut-off setting 129 where the surgeon or technician may set a maximum current level where the device 10 shuts down its electric field generation above this level.

At least two electrical outputs: phase signal 105 and common signal 107 essentially perform the surgery. Outputs may be filtered, transformed, and otherwise electrically processed through standard circuit board components to yield desired precise cell injury. Phase signal 105 passed through self-limiting conductive material electrical component 150 on to the target tissue 250. It then travels through the target tissue 250 and back to the electric field generator 100 through common signal 107. Of course, this is alternating current so it is really back and forth electron motion rather than passing through.

Self-limiting conductive material electrical component 150 regulates electrical current through the target tissue 250. As stated, self-limiting conductive material electrical component 150 functions electrically like a thermistor, thermocouple, or switch. A thermistor is a type of resistor whose resistance varies with temperature of itself. A thermocouple is an electrical component that produces a voltage that varies with its temperature and is widely used to control temperature. A switch is an electrical component that can break an electrical circuit by interrupting the current in the circuit. In all cases, self-limiting conductive material electrical component 150 regulates electrical current through the target tissue 250 as a function of its temperature.

If the case of self-limiting conductive material electrical component 150 being a switch, the alternating current in the target tissue is completely shut down by 150 for a brief period of time until the target tissue has sufficiently cooled, thereby avoiding unnecessary cell damage, and then switch 150 would switch the alternating current in the target tissue back on again, thereby heating it up again, for a brief period, only to turn off again, repeating the process. This process essentially repeats many times per second yielding an overall steady state temperature in the target tissue.

If the case of self-limiting conductive material electrical component 150 acting like a thermistor or thermocouple, the temperature changes of 150 do not lead to an abrupt off/on switching of alternating current in the target tissue, but rather yield a gradual heat increase or decrease as described below to control temperature of the target tissue and surrounding tissue. Thermistor has the most gradual fluctuations of alternating current.

Self-limiting conductive material electrical component 150 consists essentially of a homogeneous blend of different materials, including a base material and a conductor dopant. Self-limiting conductive material electrical component 150 has a special combination of base and dopant that allows the resistance of a self-limiting conductive material electrical component to vary with its temperature. As current passes through the self-limiting conductive material electrical component 150, heat is produced in the self-limiting conductive material electrical component 150 as a result of electron, ion, or other charged-particle collisions occurring inside 150 as a result of the alternating current is passing through target tissue 250. Thus, increased current through target tissue 250 yields increased heat production in self-limiting conductive material electrical component 150. This heat causes structural changes in the molecules of the homogeneous blend of material, which in turn causes a change in conductivity of self-limiting conductive material electrical component. For instance with some self-limiting conductive materials or thermistors, heat causes the base material to expand, which separates a conductive dopant suspended therein, thereby reducing, and eventual cutting off, the electrical current passing there through. In other self-limiting conductive materials or thermistors, temperature change causes a phase change of base or dopant material, which causes structural changes at the molecular level yielding a switching effect from conductive to nonconductive or vice versa.

Thermistors, thermocouples, and switches of this sort may be custom designed with a specific recipe of self-limiting conductive material to yield a specific temperature/resistance relationship and thus a specific temperature range of target area. If resistance increases with increasing temperature, the material may be called a positive temperature coefficient (PTC) thermistor or posistor. If resistance decreases with increasing temperature, the material may be called a negative temperature coefficient (NTC) thermistor. Standard resistors are designed to have constant resistance over a wide temperature range and are sometimes called zero temperature coefficient (ZTC) materials, which could be another subset of thermistor. There are many commercially available self-limiting conductive materials or thermistors that have various temperature/conductivity properties. Custom temperature/conductivity characteristics and sizes are also commercially available.

At any rate, very special care must be taken to choose/design the best self-limiting conductive material electrical component 150 to yield the best mathematical characteristics between temperature and resistance, to yield to best surgical performance, i.e. the required temperature range to cause the desired precise cell injury. The relationship between temperature and conductivity of a self-limiting conductive material electrical component is typically nonlinear, so we use log scales to describe thermistor properties. Conductivity is typically measured by the inverse of such which is resistivity.

Figure 3:
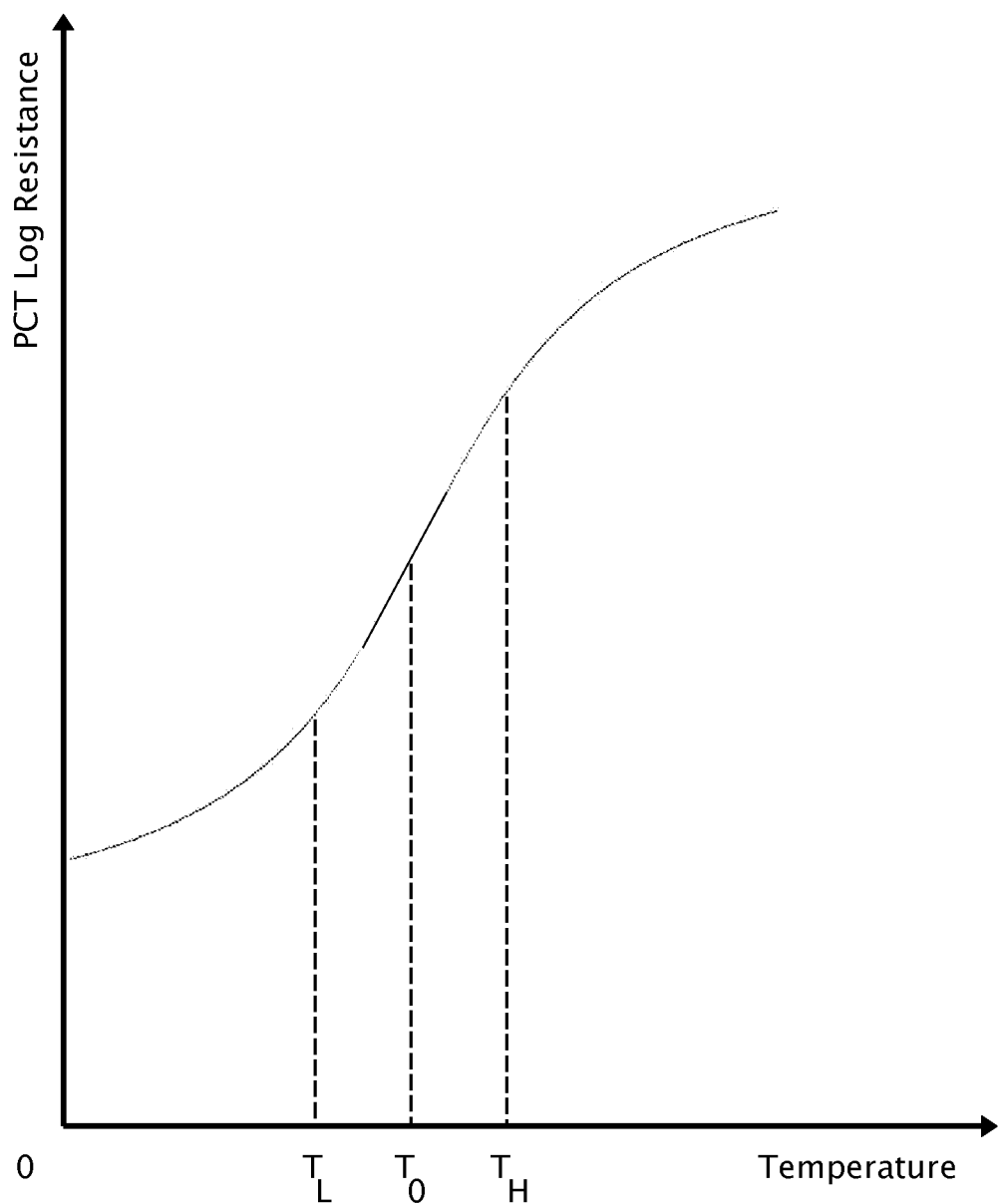
FIG. 3 is a logarithmic graph of electrical resistance (ohms) versus temperature (C) for best-mode self-limiting conductive material electrical component, which is a PTC material thermistor.

In best mode, self-limiting conductive material electrical component 150 is made of PTC material. FIG. 3 is a graph of the electrical resistivity versus temperature of a PTC heater material suitable for our purposes. Suitability for typical procedures requires a resistivity that gradually increases with temperature as noted by the mid-level positive slope character of the graph. Further, there is an inflection point in the graph at $T_0$. As temperature rises above $T_0$, resistivity increases at a decreasing rate with temperature. Thus, there is a gentle decrease at a decreasing rate of electrical current passing through the target tissue as temperature rises above $T_0$. As temperature falls below $T_0$, resistivity decreases at a decreasing rate with temperature. Thus, there is a gentle increase at a decreasing rate of electrical current passing through the target tissue as temperature falls below $T_0$. With reference to FIG. 3, going from $T_0$ to $T_H$, resistivity gradually increases, thereby decreasing heat production in the target tissue. Likewise, going from $T_0$ to $T_L$, resistivity gradually decreases, thereby increasing heat production in the target tissue. There is a mathematically stable temperature point at $T_0$, otherwise known as an inflection point. Materials with this inflection point relationship yield perfect characteristics for best mode because this yields optimal stability to keep the self-limiting conductive material electrical component very steadily set at $T_0$, thereby producing a steady alternating current in the target area.

The temperature of the self-limiting conductive material electrical component 150 determines the electrical current passing through the target area. Thus, the key design criteria of the high frequency alternating current medical device 10 is the determination of what minimum electrical current is required to produce the desired precise cell injury, then what self-limiting conductive material electrical component provides this quantity of current at it mathematical equilibrium, thereby determining the best self-limiting conductive material electrical component for the application of the high frequency alternating current medical device.

Different precise cell injury procedures may require different cell heating or electrical current operating ranges. For instance, different procedures may require different shaped and sized probes of needle-type projections 200, thereby changing current requirements, thereby changing the self-limiting conductive material electrical component requirements of the high frequency alternating current medical device 10. Different target tissues may require different current or heating thereby doing the same. Thus, certain procedures may require different self-limiting conductive material electrical component with different target temperatures $T_0$ with different operating ranges $T_H$ to $T_L$. These criteria may be adjusted by carefully choosing a PTC, NTC, or ZTC thermistor material for the high frequency alternating current medical device 10. Further, various dopants and various concentration of dopants may be used to vary characteristics to yield different resistance temperature graphs. Further combinations of PTC, NTC, and ZTC materials may be used to yield different resistance temperature graphs.

Figure 4A:
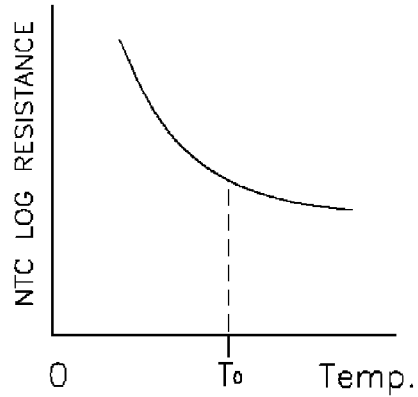
FIGS. 4A-D depict logarithmic graphs of electrical resistance (ohms) versus temperature (C) of a NTC, a ZTC, a NTC/ZTC layered material, and a PTC/ZTC layered material respectively.
Figure 4B:
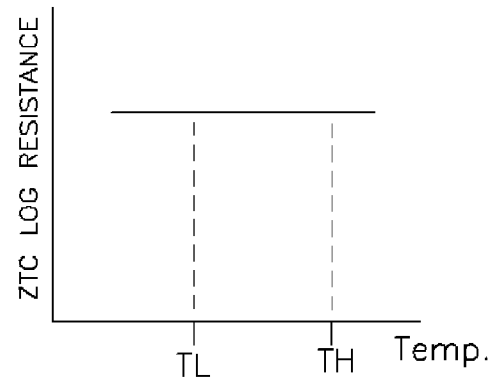
Figure 4C:
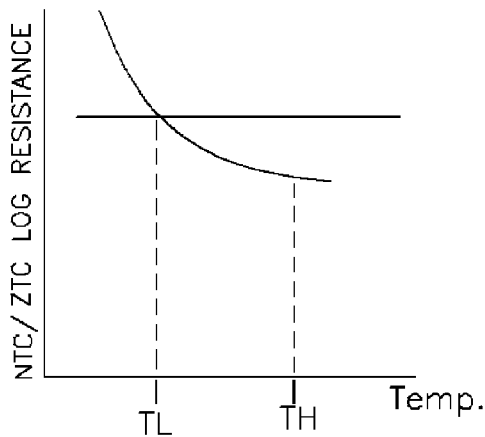
Figure 4D:
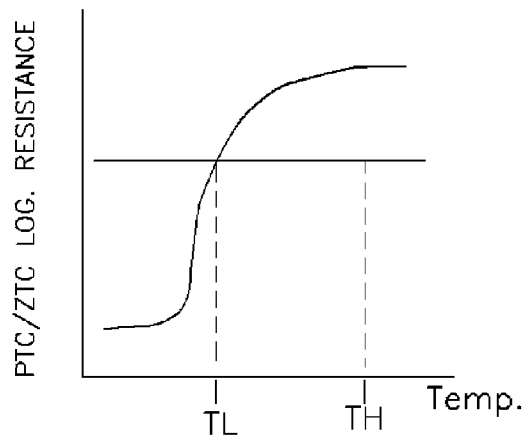
Figure 5:
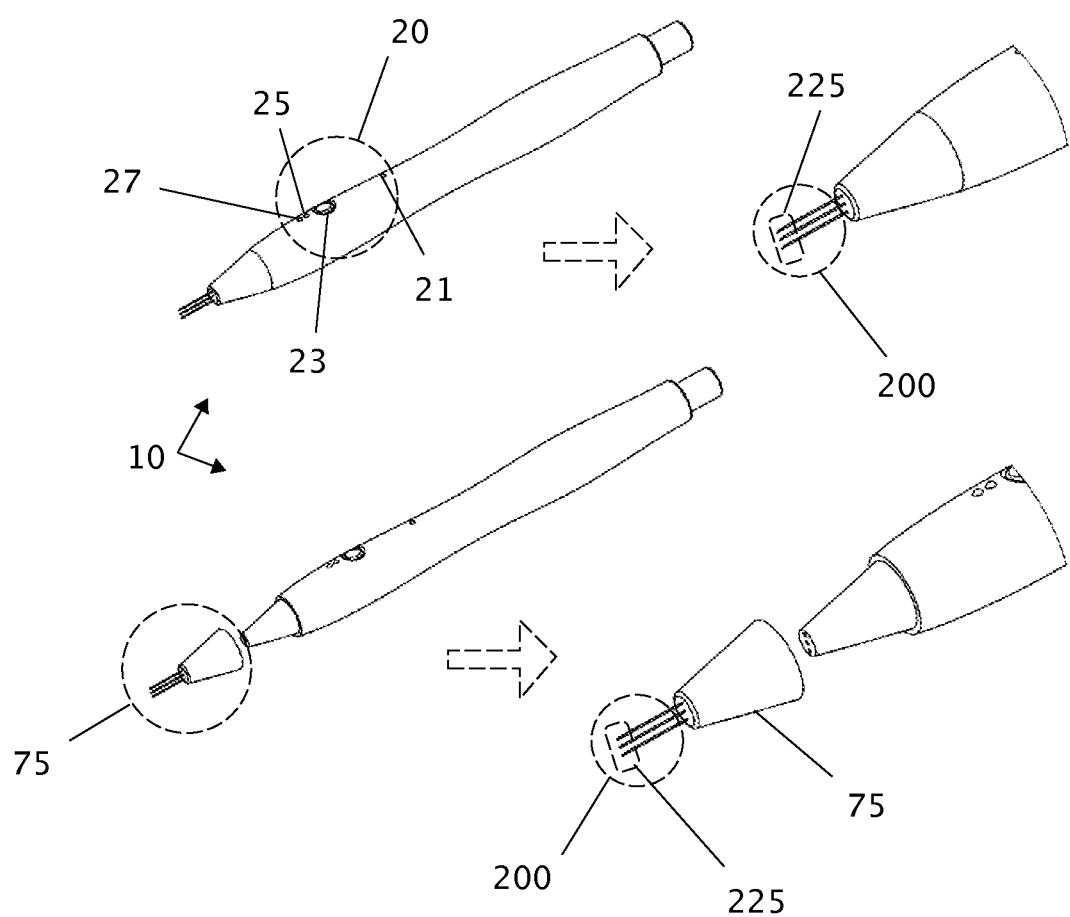
FIG. 5 shows perspective views of best mode medical device with replaceable tip attached and replaceable tip removed, with blow-up views of each.
Figure 6A:
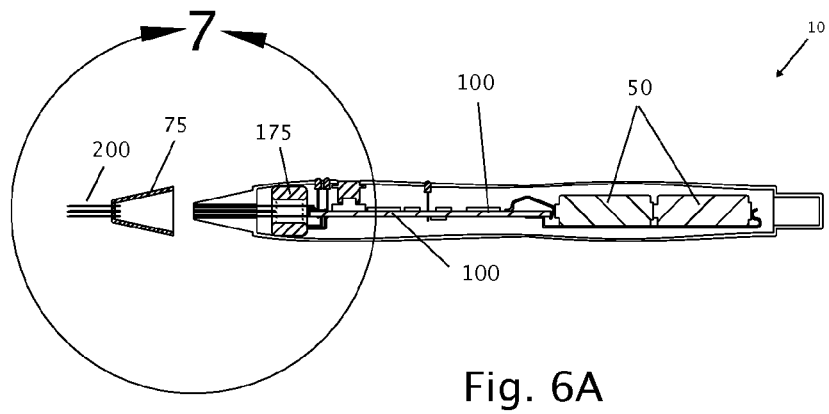
FIG. 6A is a cross-section of best mode medical device.
Figure 6B:
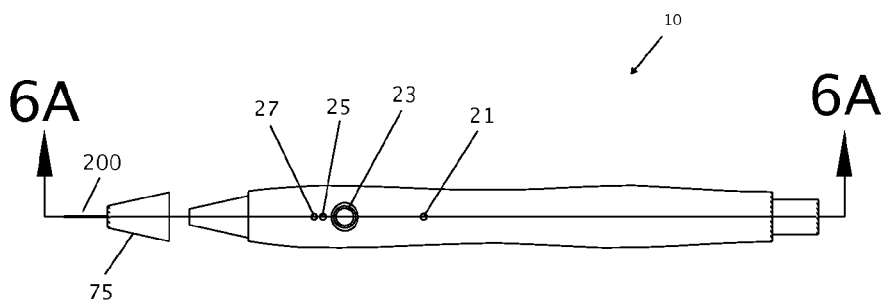
FIG. 6B is top plan view of medical device.
Figure 6C:
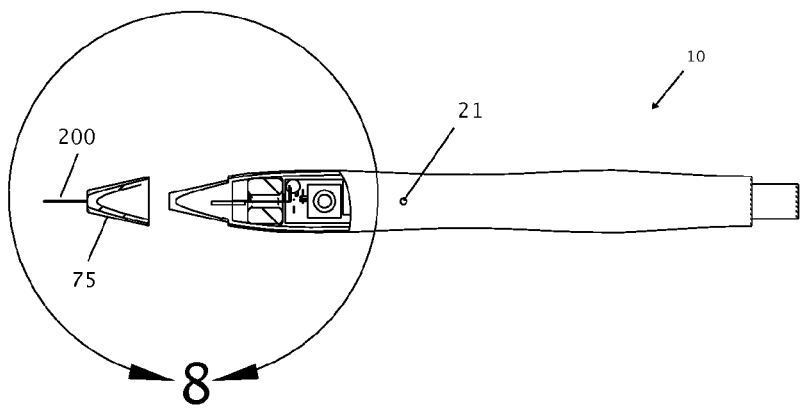
FIG. 6C is a cut-away view of FIG. 6B.
Figure 7:
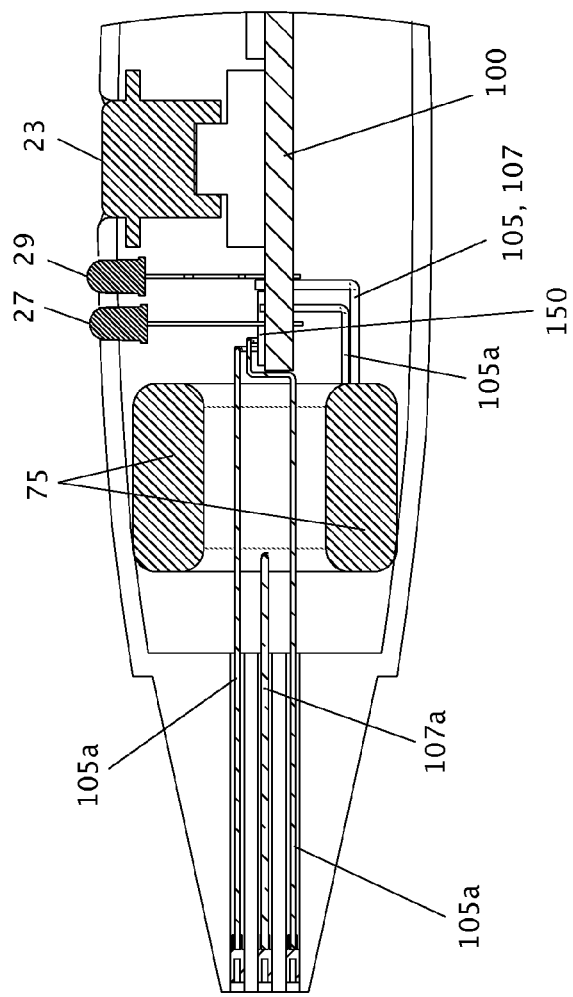
FIG. 7 is a blow-up of a side elevation view of the distal end of medical device.
Figure 7:
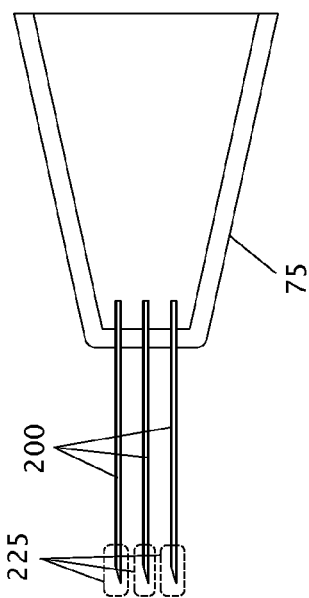
Figure 8:
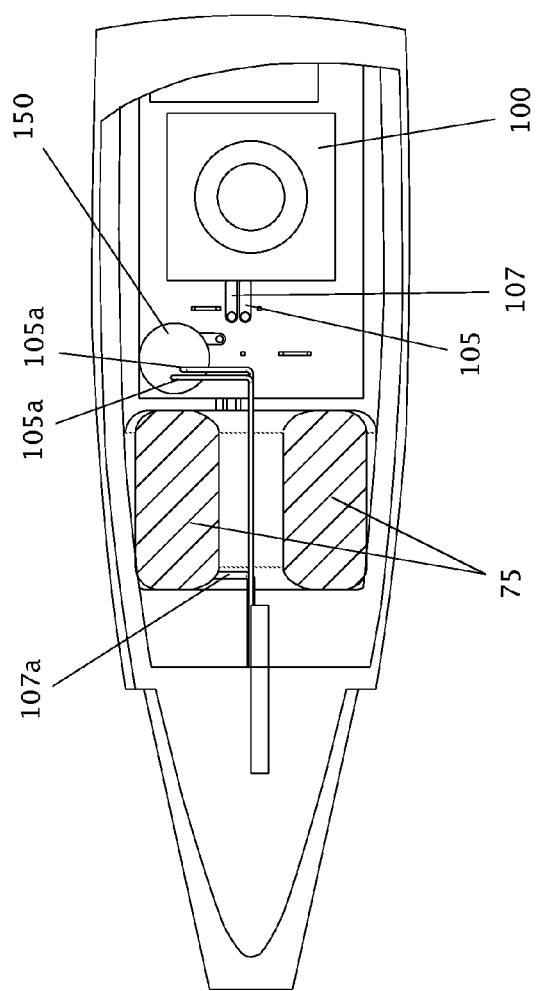
FIG. 8 is a blow-up of a top plan view of the distal end of medical device.
Figure 8:
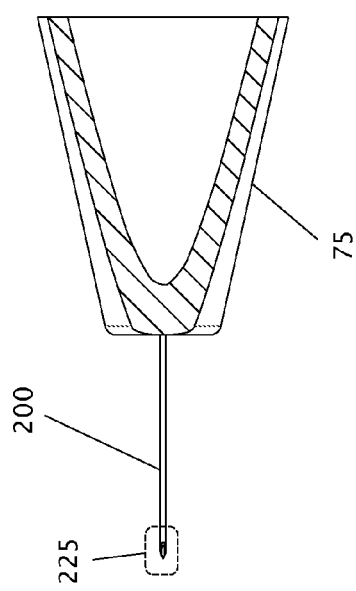

FIG. 4A includes the resistance temperature relationship of a NTC material. This arrangement may be used to create a maximum operating current as determined by temperature $T_0$ with sharp cut-off at currents above such. FIG. 4B includes the resistance temperature relationship of a ZTC material. This arrangement may be used to create constant current across the target area at a certain level across a wide range of temperatures $T_H$ to $T_L$. FIG. 4C includes the resistance temperature relationship of a NTC/ZTC material. This arrangement may be used to create a wide operating current range correlated to that of $T_H$ to $T_L$ with constant current at a certain level but with sharp cut-off at temperature $T_L$. FIG. 4D includes the resistance temperature relationship of a PTC/ZTC material. This arrangement may be used to create a wide operating current range correlated to that of $T_H$ to $T_L$ with constant current at a certain level but with sharp increase in current at temperature $T_L$ thereby preventing the target tissue a certain temperature.

PTC, NTC, and ZTC materials can be made from a crystalline or semi-crystalline polymer base material with certain conductive "doping" material added. With polymer based thermistors, transition temperature results from the melting or freezing of polymer molecules. With crystalline or semi-crystalline polymers, molecular structure is more tightly packed in solid phase and less tightly packed in amorphous phase or elastomer phase. Polymer molecules are generally non-conductive, so a conductive dopant must be added to make the material conductive. At temperatures below $T_0$, most polymer molecules are in solid phase, thus closely packed, thus at their most conductive state or level. At temperatures above $T_0$, most polymer molecules are in amorphous phase or elastomer phase, thus loosely packed, thus at their least conductive state or level. For the same choice of a matrix polymer, transition temperatures $T_0$ generally coincide with the polymer softening point of the selected matrix polymer.

Dopant material is added to base material in order to render it conductive which allows the material to perform like a heating element. Also dopant is added to slow the resistance change or to widen the graph discussed above. Dopants are conductive material such as carbon black, metal oxide, semiconductor material, blends thereof, or other material that is conductive and capable of being produced in small particles. The specific resistivity temperature relationships of PTC, NTC, and ZTC materials are arrived at by varying the type and concentration of dopant. Thus, a lower concentration or density of conductive particles in the polymer base composition is one way to obtain the desired gradual change in resistance for a self-limiting heater element. Generally speaking, dopant levels above 50 percent yield switch type material, dopant levels of 15-40% yield thermistor material, and dopant levels of 10% yield electro magnetic interference and or electrostatic discharge. Also, porosity, surface area, particle size, and oxygen content, of the conductive dopant may be varied to produce various properties. Also, more than one type of dopant may be added to base material. Either the base material molecules or the dopant material particles may actually cause the heating in the thermistor. Thus, dopant may function to produce electron transfer or vibrational heating or both. All of these factors together with various carbon black loading levels and others results in a near endless amount of combinations between type(s) and amount(s) of dopant along with type(s) of base material to yield a near endless amount of specific resistivity temperature relationships.

PTC, NTC, and ZTC materials can also be made from a ceramic material or ceramic based material with conductive dopant added. Ceramic material can be conductive or not conductive depending on phase or structure. Ceramic material can be engineered to change phase from solid to elastomer or elastomer to solid at specific temperatures $T_0$. Typically, ceramic base material is barium titanate and/or related divalent titanates and zirconates. Typical dopants include lead, strontium, rare earth metals, antimony, bismuth, or similar. Dopants are added to increase or decrease the anomaly range of the base material or further adjust the slope of the resistivity temperature relationship. Various ceramic thermistor heaters with different temperature resistivity relationships are commercially available. Also, a ceramic thermistor heater material manufacturer may endeavor to undertake special development programs to deliver specially desired characteristics.

In some modes, traditional switches are added to the tissue heating circuit or circuits or traditional thermocouples are placed near conductive segments 225 or both to further enhance temperature control of target tissue 250 or to add additional layers of safety current cut-off control or similar during electric field generation mode or surgical mode.

High frequency alternating current medical device 10 typically includes a user interface 20 comprising a main power on/off switch 21, an electric field on/off switch 23, a main power indicator light 25, and an electric field indicator light 27. User interface 20 is electrically connected to control module 125, sending and receiving signals there from, and is indirectly powered by battery 50 through control module 125 electrical connections. Main power switch 21 engages power to electric field generator inputs and to control module 125. When switch 21 is on, power indicator light 25 is illuminated. Surgery may be performed when the electric fields are generated, which is controlled by the electric field on/off switch 23. When switch 23 is activated, the electric field is engaged between the at least one probe or needle-type projection 200. Electric field indicator light 27 illuminates when electric field on/off switch 23 in engaged.

As stated, best mode high frequency alternating current medical device 10 is a hand-held battery powered single device. To facilitate this, all components are assembled onto one small circuit board. In this configuration, switches 21 and 23 may be located on the exterior of high frequency alternating current medical device 10 and at a location in close proximity to the index finger of the surgeon holding high frequency alternating current medical device 10. Lights 25 and 27 may also be located on the exterior of high frequency alternating current medical device 10. Frequency modulation setting 111 and cut-off setting 113 may be located in the interior of device 10 because they are typically set differently for certain procedures and do not need to be adjusted during the procedure.

In order to yield the most comfortably and logical instrument for a surgeon, best mode high frequency alternating current medical device 10 is shaped like a pen. The delicate nature of producing a desired precise cell injury requires fine hand movements similar to that of writing in very small print. Thus, the surgeon that is comfortable writing with a pen is also comfortable using high frequency alternating current medical device 10 to yield desired precise cell injury.

Best mode at least one probe or needle-type projection 200 has a diameter of 0.5 to 7 millimeters in outer diameter and length of 5 millimeters and up with a piercing distal end. Best mode at least one probe or needle-type projection 200 primarily has a non-conductive surface that is not electrically connected to signal outputs 105 or 107 and thus does not emit an electric field except for at certain segments 225 of the probe or needle-type projection 200. Only at segments 225 will an electric field emit there from. As stated, at least two conductive segments 225 are required to generate electrical current in target tissue. In the most two basic modes of high frequency alternating current medical device 10, at least two conductive segments 225 are both located on one probe or needle-type projection 200 or one segment 225 is located on each of two needle-type projections 200. Conductive segments 225 may have a layer or coating or alternately may not have a layer or coating that causes segments 225 to be conductive. For instance, the needles may be made of nonconductive material where conductive segments are formed by one or more conductive coatings thereon. Needles may be made of conductive material with nonconductive coatings on the surface except at conductive segments 225. Any assembly of conductive and nonconductive materials may be used to yield needles/probes with effective conductive segments 225. Segments 225 are electrically connected to signals 105 or 107. When segments 225 are located on the distal ends of probes or needle-type projections 200, heat is produced below the surface of the tissue only, thereby providing much more opportunity to cause the desired precise cell injury without also changing the surface of the tissue. In best mode, segments 225 are located at the distal ends of needle-type projections 200 and are about 1-4 millimeters in length.

The method of using said high frequency alternating current medical device 10 comprises the steps of: picking up said high frequency alternating current medical device 10, turning on said high frequency alternating current medical device, touching said at least one probe or needle-type projection 200 to the surface of target tissue 250, inserting said at least one probe or needle-type projection 200 beneath the surface of target tissue 250, or inserting said at least one probe or needle-type projection 200 into a body cavity 250, engaging said electric field generator 100 thereby inducing or generating an electrical alternating current in target tissue 250, disengaging the electric field generator 100, removing said at least one probe or needle-type projection 200 from said target tissue 250, and repeating the former steps as necessary to cause the desired certain desired precise cell injury.

A high frequency alternating current medical device constructed according to the present invention may be used by touching at least one probe or needle-type projection 200 to target tissue 250, whether on the skin surface of a patient, subcutaneously or deeper. If the target tissue is skin or subcutaneous tissue, a specific type of probe and temperature may be chosen to achieve skin tightening, resurfacing or collagen remodeling. The maintenance temperature of the device could be chosen to be not more than 41° C. (106° F.). At such a moderate temperature 200 can produce skin tightening, skin resurfacing and collagen remodeling, for dermal regeneration and cosmetic applications. This can also be accompanied by mechanical ablation of skin surface cells. Alternatively, a higher temperature could be used to cut skin, while simultaneously cauterizing any bleeding.

If the target tissue is subcutaneous adipose (fat) tissue, 200 must have piercing structure to be inserted into the skin to cause selective damage to fat cells proximate to the end of 200.

The target tissue might be glandular, as in sweat glands of the skin to treat hyperhidrosis or the tonsils in the oral cavity in performing a total or partial tonsillectomy.

The target tissue could be vascular (veins, arteries, capillaries, blood), wherein heat transfer through the probe can be used to produce local blood coagulation and cauterization of the vascular tissue. Or, at more gentle temperatures (near 37° C. body temperature), a hollow probe can inject a pre-heated fluid into the target artery or vein, e.g., for localized drug delivery.

The target tissue could be some abnormal growth, polyp or tumor, such as in the sinus or oral cavity. Here, heat transfer through the probe can ablate that tissue. Examples include: mucosal lesions found in Barrett's esophagitis, or tissue growth from nasal turbinate hypertrophy, or removal of colon or rectal polyps.

The target tissue might be any organ system in the body, such as heart, lungs, brain, eyes, kidney, liver, ovaries, thyroid, bladder, uterus, stomach, intestines, appendix, gall bladder, or similar.

What is claimed is:
1. A high frequency alternating current medical device comprising:
   an electrical power source;
   an electric field generator;
   a self-limiting conductive material electrical component;
   at least one probe or needle-type projection; and
   at least two conductive segments, wherein,
      said at least one probe or needle-type projection is located at the distal end of said high frequency alternating current medical device and is capable of being inserted to tissue or a body cavity,
      said at least two conductive segments are located on said at least one probe or needle-type projection,
      said at least two conductive segments are capable of electrically connecting to an electrically conductive foreign medium in contact with said at least one probe or needle-type projection,
      said at least two conductive segments are electrically connected to said electric field generator, said electric field generator is electrically connected to said electrical power source,
      said electric field generator is capable of producing at least one phase signal wave output and at least one common signal wave output, said at least one phase signal wave output is electrically connected to one or more said at least two conductive segments and said at least one common signal wave output is electrically connected to one or more said at least two conductive segments, such that each of said at least two conductive segments is electrically connected to either a phase signal wave output and a common signal wave output, said at least one phase signal wave output and at least one common signal wave output are capable of producing an alternating polarity electric field between said at least two conductive segments, wherein said alternating polarity electric field may induce an electrical alternating current between said at least two conductive segments when contacted by electrically conductive outside material such as human or animal tissue, said self-limiting conductive material electrical component is placed in electrical series connection between said electric field generator and said at least one phase signal output, and said self-limiting conductive material electrical component consists primarily of: a polymer base material with 5-40% conductive dopant material, a ceramic base material with 1-40% conductive dopant material, or a ceramic material without dopant material, wherein, said self-limiting conductive material electrical component is characterized by an electrical resistance that varies with temperature.

2. The high frequency alternating current medical device as recited in claim 1, wherein said electrical power source is a direct current battery of any voltage or an alternating current power source of any voltage.

3. The high frequency alternating current medical device as recited in claim 1, wherein said a self-limiting conductive material electrical component is made primarily of: positive temperature coefficient material; negative temperature coefficient material; zero temperature coefficient material; a combination of zero temperature coefficient material and negative temperature coefficient material; or a combination of zero temperature coefficient material and positive temperature coefficient material.

4. The high frequency alternating current medical device as recited in claim 3, wherein said self-limiting conductive material electrical component is a thermistor, thermocouple, or switch.

5. The high frequency alternating current medical device as recited in claim 4, wherein all components of said high frequency alternating current medical device are assembled inside a small handheld enclosure.

6. The high frequency alternating current medical device as recited in claim 5, wherein said small handheld enclosure is oblong-shaped.

7. A high frequency alternating current medical device as recited in claim 6, wherein said small handheld enclosure has exterior surfaces shaped like a pen or a mechanical pencil or marker.

8. The high frequency alternating current medical device as recited in claim 5 with two probes or needle-type projections and two conductive segment where each probe or needle-type projection has one conductive segment located thereon.

9. The high frequency alternating current medical device as recited in claim 5 with three probes or needle-type projections and three conductive segments where each probe or needle-type projection has one conductive segment located thereon.

10. The high frequency alternating current medical device as recited in claim 1, wherein said at least one probe or needle-type projection and at least two conductive segments located thereon are removably attachable to the rest of said high frequency alternating current medical device wherein said at least one probe or needle-type projection can be attached and locked into place, electrically connecting said at least two conductive segments to said at least one phase signal wave output or said at least one common signal wave output to that surgery may be performed, and then unlocked and removed from said high frequency alternating current medical device.

11. The high frequency alternating current medical device as recited in claim 1, wherein at least one probe or needle-type projection is needle-shaped with an outside diameter of 0.5 to 7 millimeters.

12. The high frequency alternating current medical device as recited in claim 1, wherein at least one probe or needle-type projection has cross-sectional shape that is circular, oval, square, rectangular, or oblong.

13. The high frequency alternating current medical device as recited in claim 1, wherein at least one probe or needle-type projection has a distal end that is: rounded, roller-balled, piercing, pointed, or blunt.

14. A method of using a high frequency alternating current medical device comprising:
 a) obtaining a high frequency alternating current medical device having at least one probe or needle-type projection with at least two conductive segments;
 b) switching on said high frequency alternating current medical device, including electrically coupling a electrical power supply to a electric field generator;
 c) touching a distal end of said at least one probe or needle-type projection to a surface of a target tissue, inserting the distal end of said at least one probe or needle-type projection beneath the surface of the target tissue, or inserting the distal end of said at least one probe or needle-type projection into a body cavity containing a target tissue;
 e) switching on said electric field generator, including electrically coupling each of said at least two conductive segments to at least one of a phase signal wave output and a common signal wave output, thereby generating an alternating polarity electric field between said at least two conductive segments;
 f) switching off said electric field generator, including electrically decoupling each of said at least two conductive segments from said electric field generator;
 g) adjusting or repositioning the distal end of said at least one probe or needle-type projection on or in said target tissue;
 h) switching on said electric field generator, including electrically coupling each of said at least two conductive segments to said electric field generator to either said at least one phase signal wave output or said at least one common signal wave output, thereby generating an alternating polarity electric field between said at least two conductive segments;
 i) switching off said electric field generator, including electrically decoupling each of said at least two conductive segments from said electric field generator;
 j) repeating steps g through i until a desired precise cell injury is attained; and
 k) removing the distal end of said at least one probe or needle-type projection from said target tissue.

15. The method of claim 14 further comprising the following steps inserted after step (a):
 removing said at least one probe or needle-type projections with said at least two conductive segments located thereon from the rest of said high frequency alternating current medical device, wherein said at least one probe or needle-type projections with said at least two conductive segments located thereon is removably attachable to the rest of said high frequency alternating current medical device;

choosing from a set of said at least one probe or needle-type projections with said at least two conductive segments located thereon, wherein each of said set has a different shaped said at least one probe or needle-type projections that may be appropriate for a certain type or size of target cell and certain type of desired precise cell injury;

attaching said chosen at least one probe or needle-type projections with said at least two conductive segments located thereon to the rest of said high frequency alternating current medical device using an attachment means that is reversible and lockable so that when attached said at least one probe or needle-type projection is solidly connected to the rest of said high frequency alternating current medical device and required electrical connections are completed so that surgery may be performed; and completing steps (b) through (k).

16. The method of claim 14 or 15, wherein said step of touching the distal end of at least one probe or needle-type projection to a target tissue, piercing the distal end of at least one probe or needle-type projection into a target tissue, or inserting the distal end of at least one probe or needle-type projection into a body cavity containing a target tissue forms part of a pain management or treatment protocol.

17. The method of claim 14 or 15, wherein said target tissue is skin and said desired precise cell injury is skin tightening, skin resurfacing, collagen remodeling, tissue cutting, tissue ablation, or pain relief.

18. The method of claim 14 or 15, wherein said target tissue is subcutaneous adipose tissue and said desired precise cell injury is selective damage to fat cells proximate to said at least one probe or needle-type projection.

19. The method of claim 14 or 15, wherein said target tissue is nerve tissue and said desired precise cell injury is ablation of nerve tissue yielding wrinkle relaxation, pain relief, muscle twitch or spasm relief, or repair of cardiac electrical conduction abnormalities.

20. The method of claim 14 or 15, wherein said target tissue is a rami of the temporal branch of the facial nerve or the angular nerve supplying innervations to the corrugator and procerus muscles of the face.

21. The method of claim 14 or 15, wherein said target tissue is glandular including sweat glands of the skin or tonsils of the oral cavity.

22. The method of claim 14 or 15, wherein said target tissue is vascular tissue and said desired precise cell injury is blood coagulation and cauterization of the vascular tissue or ablation or shrinkage of atherosclerotic plaques in blood vessels.

23. The method of claim 14 or 15, wherein said target tissue is polyp, tumor, lesion, or abnormal growth and said desired precise cell injury is ablation said target tissue.

24. The method claim 14 or 15, wherein said target tissue is selected from the group consisting of epidermis skin, dermis skin, mucosal lining, cartilage, muscle, bone, tendons, ligaments, central nervous system, brain, spine, peripheral nervous system, heart, liver, stomach, kidney, bladder, prostate, lungs, intestines, gallbladder, appendix, spleen, brain, tongue, orbits, ocular tissue, auditory system, teeth, tonsils, adenoids, salivary glands, uterus, ovaries, testicular tissue, nasal or sinus tissue, thyroid, parathyroids, pancreas, adrenal glands, pharynx, larynx, esophagus, rectum, lymphatic tissue, and vascular tissue.

* * * * *